US012102816B2

(12) United States Patent
Kusano et al.

(10) Patent No.: US 12,102,816 B2
(45) Date of Patent: Oct. 1, 2024

(54) CONDUIT FORMING UNIT AND TUBE JOINT

(71) Applicant: SUN MEDICAL TECHNOLOGY RESEARCH CORPORATION, Nagano (JP)

(72) Inventors: Eisuke Kusano, Nagano (JP); Naofumi Miyajima, Nagano (JP)

(73) Assignee: SUN MEDICAL TECHNOLOGY RESEARCH CORPORATION, Nagano (JP)

( * ) Notice: Subject to any disclaimer, the term of this patent is extended or adjusted under 35 U.S.C. 154(b) by 904 days.

(21) Appl. No.: 17/268,422

(22) PCT Filed: Aug. 24, 2018

(86) PCT No.: PCT/JP2018/031436
§ 371 (c)(1),
(2) Date: Feb. 12, 2021

(87) PCT Pub. No.: WO2020/039592
PCT Pub. Date: Feb. 27, 2020

(65) Prior Publication Data
US 2021/0346681 A1   Nov. 11, 2021

(51) Int. Cl.
| | |
|---|---|
| A61M 60/859 | (2021.01) |
| A61M 25/00 | (2006.01) |
| A61M 60/178 | (2021.01) |
| A61M 60/216 | (2021.01) |
| A61M 60/857 | (2021.01) |
| A61M 60/861 | (2021.01) |
| F16L 19/02 | (2006.01) |
| F16L 19/025 | (2006.01) |

(52) U.S. Cl.
CPC ...... *A61M 60/859* (2021.01); *A61M 25/0009* (2013.01); *A61M 60/178* (2021.01);
(Continued)

(58) Field of Classification Search
CPC .......................... A61M 60/855–60/859; A61M 60/178–60/183; A61M 60/861; A61M 39/12; A61M 39/10
See application file for complete search history.

(56) References Cited

U.S. PATENT DOCUMENTS 9,821,099 B2 * 11/2017 Miyakoshi .......... A61M 60/859
11,724,090 B2 * 8/2023 Phillips ............... A61M 60/122
623/3.26
(Continued)

FOREIGN PATENT DOCUMENTS

JP   H66868 U    1/1994
JP   5899528 B2  4/2016

OTHER PUBLICATIONS

International Search Report in PCT/JP2018/031436, mailed Oct. 23, 2018, 2pp.

*Primary Examiner* — Alvin J Stewart
(74) *Attorney, Agent, or Firm* — HAUPTMAN HAM, LLP

(57) ABSTRACT

A conduit forming unit includes: a cylindrical tubular body having flanges, on both end portions of the cylindrical tubular body; a first connection tubular body and a second connection tubular body respectively connected to a first end portion and a second end portion of the cylindrical tubular body; and tube joints for connecting the cylindrical tubular body and the first connection tubular body and the second connection tubular body to each other. The tube joint includes: a pawl equipped nut where a plurality of pawl portions which are engageable with the flange of the cylindrical tubular body are formed in the pawl equipped nut, the pawl portions engage with the flange so as to connect the first connection tubular body and the cylindrical tubular body to each other; and a retaining ring being annularly (Continued)

mountable on the pawl equipped nut and retaining engagement of the pawl portions with the flange.

9 Claims, 6 Drawing Sheets

(52) U.S. Cl.
CPC ........ *A61M 60/216* (2021.01); *A61M 60/857* (2021.01); *A61M 60/861* (2021.01); *F16L 19/0218* (2013.01); *F16L 19/025* (2013.01)

(56) References Cited

U.S. PATENT DOCUMENTS

| | | | |
|---|---|---|---|
| 11,745,004 B1* | 9/2023 | Beltr!n Calva | A61M 60/178 600/16 |
| 2008/0221469 A1* | 9/2008 | Shevchuk | F16L 33/23 96/10 |
| 2008/0306328 A1* | 12/2008 | Ercolani | A61M 60/857 600/16 |
| 2013/0060268 A1* | 3/2013 | Herrig | A61M 60/37 606/153 |
| 2017/0049944 A1 | 2/2017 | Kinoshita et al. | |
| 2019/0160212 A1* | 5/2019 | Arslan | A61M 60/178 |
| 2019/0184151 A1* | 6/2019 | Herrig | A61M 39/1011 |
| 2019/0201600 A1* | 7/2019 | Schade | A61M 60/178 |
| 2019/0201601 A1* | 7/2019 | Motomura | A61M 60/585 |
| 2020/0000987 A1* | 1/2020 | Phillips | A61M 39/10 |
| 2020/0086021 A1* | 3/2020 | Jeevanandam | A61M 60/857 |
| 2020/0246528 A1* | 8/2020 | Mortis | A61M 60/857 |
| 2020/0368413 A1* | 11/2020 | Phillips | A61M 60/859 |
| 2021/0361932 A1* | 11/2021 | Roelle | A61M 60/861 |
| 2022/0296874 A1* | 9/2022 | Tsui | A61M 60/32 |
| 2022/0323743 A1* | 10/2022 | Morello | A61M 60/178 |
| 2022/0362562 A1* | 11/2022 | Nguyen | A61M 60/178 |
| 2024/0157119 A1* | 5/2024 | Snyder | A61M 60/178 |

\* cited by examiner

CONDUIT FORMING UNIT AND TUBE JOINT

RELATED APPLICATIONS

The present application is a National Phase of International Application No. PCT/JP2018/031436 filed Aug. 24, 2018.

TECHNICAL FIELD

The present invention relates to a conduit forming unit and a tube joint.

BACKGROUND ART

As a medical equipment which is used for a patient with a severe heart failure, there has been known a ventricular assist system which compensates for a portion of a function of a heart (see patent literature 1, for example).

FIG. 7 is a view for describing a ventricular assist system 800 described in patent literature 1. As shown in FIG. 7, the ventricular assist system 800 described in patent literature 1 includes: a blood pump 810 embedded in a human body; artificial blood vessels 830, 840 for connecting the blood pump 810 and a heart 820 to each other; a controller (not shown in the drawing) having a function of controlling the blood pump 810 outside the human body; and a connection cable 850 for ventricular assist disposed between the blood pump 810 and the controller.

With respect to the artificial blood vessels 830, 840, the artificial blood vessel 830 is an artificial blood vessel which allows blood flowing out from a left ventricle of the heart 820 to flow into the blood pump 810. The artificial blood vessel 830 is also referred to as an inflow side artificial blood vessel. On the other hand, the artificial blood vessel 840 is an artificial blood vessel which supplies blood from the blood pump 810 to an ascending aorta. The artificial blood vessel 840 is also referred to as an outflow side artificial blood vessel. Accordingly, the artificial blood vessel 830 is also expressed as an inflow side artificial blood vessel 830, and the artificial blood vessel 840 is also expressed as an outflow side artificial blood vessel 840. The inflow side artificial blood vessel 830 is connected to the heart 820 through a cannula (not shown in the drawing).

The inflow side artificial blood vessel 830 and the outflow side artificial blood vessel 840 used in such a ventricular assist system 800 are conventionally formed using various materials. For example, an expanded polytetrafluoroethylene (ePTFE) is one of such materials. As the inflow side artificial blood vessel 830 and the outflow side artificial blood vessel 840, there has been known a vessel having the configuration where a cylinder is formed using such a material having flexibility, and a wire made of PTFE or the like is spirally wound around the cylinder.

In this manner, the inflow side artificial blood vessel 830 and the outflow side artificial blood vessel 840 have the configuration where the wire made of PTFE or the like is spirally wound around the cylinder. Accordingly, the inflow side artificial blood vessel 830 and the outflow side artificial blood vessel 840 have an effect of preventing twisting, collapsing, bending and the like while maintaining flexibility. However, to ensure reliability as artificial blood vessels, it is important for the inflow side artificial blood vessel 830 and the outflow side artificial blood vessel 840 to further increase an effect of preventing twisting, collapsing, bending and the like.

Particularly, a negative pressure is liable to be generated in the inflow side artificial blood vessel 830 and hence, the inflow side artificial blood vessel 830 is liable to be collapsed. In view of the above, recently, an attempt has been made to form a cylindrical tubular body made of a material having high rigidity as a material of the inflow side artificial blood vessel 830, and to use such a cylindrical tubular body as the inflow side artificial blood vessel. Metal can be exemplified as the material having high rigidity. Among metals, titanium or the like having excellent corrosion resistance and excellent compatibility with a living tissue can be preferably used.

When a cylindrical tubular body made of metal is used as the inflow side artificial blood vessel 830, the cylindrical tubular body made of metal is interposed between the heart and the blood pump. In this case, a connection tubular body (referred to as a first connection tubular body) which functions as a cannula is connected to a first end portion side (an end portion positioned on a heart 820 side) of the circular tubular body, and a connection tubular body (referred to as a second connection tubular body) mounted on the blood pump 810 is connected to a second end portion side (an end portion positioned on a blood pump 810 side) of the cylindrical tubular body. The second connection tubular body may be integrally formed with the blood pump.

The first connection tubular body which functions as the cannula, the cylindrical tubular body which forms the inflow side artificial blood vessel 830 and the second connection tubular body disposed on the blood pump side can be regarded as a conduit for supplying blood from the heart to the blood pump. It is important for such a conduit to possess liquid tightness. As a method for forming a conduit having liquid tightness, for example, a technique is considered where a flange is formed on each of both end portions (the first end portion and the second end portion on a side opposite to the first end portion) of a cylindrical tubular body, the cylindrical tubular body and the first connection tubular body are brought into close contact with each other using a dedicated tube joint, and the cylindrical tubular body and the second connection tubular body are brought into close contact with each other using the dedicated tube joint.

An example having the above-mentioned configuration where the cylindrical tubular body on which the flange is formed on each of both end portions and the other cylindrical tubular body (the first connection tubular body or the second connection tubular body in the above-mentioned case) are connected to each other using the dedicated tube joints is described in patent literature 2.

FIG. 8 is a view for describing a tube joint 900 described in patent literature 2. The tube joint 900 described in patent literature 2 is not a tube joint used for a ventricular assist system, but is a tube joint for forming a conduit for hydraulic piping. In FIG. 8, an example is shown where a cylindrical tubular body 930 having one end portion (first end portion) on which a flange 932 is formed and an adapter 910 which constitutes another tubular body are connected to each other using a cap nut 920. On the other end portion (second end portion) of the cylindrical tubular body 930, a protruding portion 933 having substantially the same shape as a flange is formed although it is indefinite whether the protruding portion 933 functions as the flange.

With respect to the tube joint 900 described in patent literature 2, the cap nut 920 is annularly mounted on the outer peripheral surface 931 of the cylindrical tubular body 930 in a slidable manner along the outer peripheral surface 931 and, thereafter, female threads 921 of the cap nut 920 threadedly engage with male threads 911 of the adapter 910 thus fastening the cap nut 920. Accordingly, the flange 932 formed on one end portion (first end portion) of the cylindrical tubular body 930 is pressed in a direction toward the adapter 910 by a bottom portion 922 of the cap nut 920 so that the flange 932 is brought into pressure contact with the adapter 910. An O-ring 940 is interposed between the flange 932 of the cylindrical tubular body 930 and the adapter 910. With such a configuration, the cylindrical tubular body 930 can be connected to the adapter 910 in a liquid tight state.

CITATION LIST

Patent Literature

Patent literature 1: Japanese Patent No. 5899528

Patent literature 2: JP 6-6868 U

SUMMARY OF INVENTION

Technical Problem

However, in the tube joint 900 described in patent literature 2, as described above, the flange 932 is formed on one end portion (first end portion) of the cylindrical tubular body 930, and the protruding portion 933 having substantially the same shape as the flange is formed on the other end portion (second end portion) of the cylindrical tubular body 930. Accordingly, it is considered difficult to annularly mount the cap nut 920 on the cylindrical tubular body 930. However, with respect to the tube joint 900 described in patent literature 2, the manner of annularly mounting the cap nut 920 on the cylindrical tubular body 930 is not explicitly described.

Accordingly, even when one wants to use the tube joint 900 described in patent literature 2 as tube joints for connecting, for example, a first connection tubular body which functions as a cannula, the cylindrical tubular body which constitutes the inflow side artificial blood vessel 830 where the flange is formed on each of both end portions in a protruding manner, and the second connection tubular body disposed on a blood pump side to each other, these first connection tubular body, the cylindrical tubular body and the second connection tubular body cannot be connected to each other. Accordingly, it is considered that a conduit constituted of the first connection tubular body, the cylindrical tubular body and the second connection tubular body cannot be formed.

The present invention has been made in view of the above-mentioned circumstances, and it is an object of the present invention to provide a conduit forming unit where a cylindrical tubular body in which flanges are respectively formed on a first end portion and a second end portion on a side opposite to the first end portion in a protruding manner, a first connection tubular body disposed on a first end portion side of the cylindrical tubular body, and a second connection tubular body disposed on a second end portion side of the cylindrical tubular body can be connected to each other using tube joints so that a conduit constituted of the first connection tubular body, the cylindrical tubular body and the second connection tubular body can be formed. It is another object of the present invention to provide a tube joint which can be used in such a conduit forming unit.

Solution to Problem

[1] A conduit forming unit according to the present invention includes: a cylindrical tubular body where flanges are respectively formed on an outer peripheral surface of a first end portion of the cylindrical tubular body and on an outer peripheral surface of a second end portion of the cylindrical tubular body on a side opposite to the first end portion in an axial direction of a tubular body, the flanges being integrally formed on the tubular body in a protruding manner toward an outer side in a radial direction; a first connection tubular body disposed on a first end portion side of the cylindrical tubular body, and having male threads on an outer peripheral surface of the first connection tubular body; a second connection tubular body disposed on a second end portion side of the cylindrical tubular body, and having male threads on an outer peripheral surface of the second connection tubular body; a tube joint which connects the cylindrical tubular body and the first connection tubular body to each other; and a tube joint which connects the cylindrical tubular body and the second connection tubular body to each other, wherein both the tube joint and the tube joint each include: a cylindrical pawl equipped nut where female threads which are threadedly engageable with the male threads formed on the first connection tubular body or the male threads formed on the second connection tubular body are formed on an inner peripheral surface of the cylindrical pawl equipped nut, a plurality of pawl portions which are engageable with either of the flanges of the cylindrical tubular body are formed in the cylindrical pawl equipped nut in a circumferential direction and in a protruding manner toward an inside in a radial direction, the plurality of pawl portions are configured to get over either of the flanges of the cylindrical tubular body and to engage with either of the flanges, and the female threads are configured to threadedly engage with the male threads of the first connection tubular body or the male threads of the second connection tubular body so as to bring about a fastening state of the cylindrical pawl equipped nut thus enabling connection between the first connection tubular body and the cylindrical tubular body or connection between the second connection tubular body and the cylindrical tubular body; and a retaining ring being annularly mountable on an outer peripheral surface of the pawl equipped nut, the retaining ring being capable of retaining engagement of the plurality of pawl portions with either of the flanges of the cylindrical tubular body, and the plurality of pawl portions of the pawl quipped nut are each formed on each of distal end portions of a plurality of protruding lugs formed on the pawl equipped nut in a protruding manner in an axial direction at a predetermined interval in a circumferential direction, and the plurality of protruding lugs have elasticity in a radial direction, and the retaining ring is annularly mounted on the plurality of protruding lugs, and the retaining ring is configured to impart a pressing force to the plurality of pawl portions in a radial direction in a state where the retaining ring is annularly mounted on the plurality of protruding lugs.

The conduit forming unit according to the present invention has the above-mentioned configuration. Accordingly, the cylindrical tubular body where the flanges are respectively formed on the first end portion and the second end portion on a side opposite to the first end portion in a protruding manner, the first connection tubular body disposed on the first end portion side of the cylindrical tubular body, and the second connection tubular body disposed on the second end portion side of the cylindrical tubular body can be connected to each other using the tube joints. As a result, it is possible to form a conduit which is constituted of the first connection tubular body, the cylindrical tubular body and the second connection tubular body.

In connecting the first connection tubular body and the cylindrical tubular body to each other, the first connection tubular body and the cylindrical tubular body can be connected to each other such that a rotational force about an axis is not applied to the first connection tubular body, and a rotational force about an axis is also not applied to the cylindrical tubular body. In the same manner, also in connecting the second connection tubular body and the cylindrical tubular body to each other, the second connection tubular body and the cylindrical tubular body can be connected to each other such that a rotational force about an axis is not applied to the second connection tubular body, and a rotational force about an axis is also not applied to the cylindrical tubular body.

For example, the case where the first connection tubular body and the cylindrical tubular body are connected to each other is described as an example. The first connection tubular body is pressed by a hand or the like in a state where the cylindrical pawl equipped nut engages with the flange of the cylindrical tubular body. In such a state, the cylindrical pawl equipped nut which is in engagement with the flange of the cylindrical tubular body is made to slide toward a rear side along an outer peripheral surface of the first connection tubular body so that the female threads of the cylindrical pawl equipped nut threadedly engage with the male threads of the first connection tubular body whereby the cylindrical pawl equipped nut can be fastened. In performing such an operation, a fastening operation of the cylindrical pawl equipped nut can be performed without moving the first connection tubular body and the cylindrical tubular body. This is because the cylindrical pawl equipped nut is not stopped with respect to the cylindrical tubular body by thread engagement but is simply configured such that the pawl portions are made to engage with the flange. The same operation is performed in connecting the second connection tubular body and the cylindrical tubular body to each other.

[2] In the conduit forming unit according to the present invention, it is preferable that the first connection tubular body be connected to a left ventricle of a heart of a living body, and have a function of guiding blood flowing out from the left ventricle of the heart to the cylindrical tubular body, and the second connection tubular body be provided to a blood pump of a ventricular assist system, and have a function of allowing the blood flowing out from the cylindrical tubular body to flow into the blood pump.

In this manner, the conduit forming unit according to the present invention can be used in the ventricular assist system. That is, the conduit forming unit can be used for connecting the first connection tubular body which is connected to the left ventricle of the heart and the cylindrical tubular body which functions as the artificial blood vessel to each other. The conduit forming unit can be also used for connecting the second connection tubular body which is provided to the blood pump and the cylindrical tubular body which functions as the artificial blood vessel to each other.

[3] In the conduit forming unit according to the present invention, it is preferable that the cylindrical tubular body, the first connection tubular body and the second connection tubular body and the tube joints be each formed of a non-flexible rigid member.

In this manner, the cylindrical tubular body, the first connection tubular body and the second connection tubular body are each formed of the non-flexible rigid member and hence, it is possible to acquire an effect of preventing twisting, collapsing, bending and the like of the cylindrical tubular body, the first connection tubular body and the second connection tubular body. The cylindrical tubular body, the first connection tubular body and the second connection tubular body form the conduit. Accordingly, even if a negative pressure is generated in the conduit, since the cylindrical tubular body, the first connection tubular body and the second connection tubular body are each formed of a non-flexible rigid member, it is possible to prevent the occurrence of twisting, collapsing, bending and the like of the cylindrical tubular body, the first connection tubular body and the second connection tubular body.

[4] In the conduit forming unit according to the present invention, it is preferable that the non-flexible rigid member be made of metal.

With such a configuration, it is possible to increase an effect of preventing twisting, collapsing, bending and the like of the cylindrical tubular body, the first connection tubular body and the second connection tubular body. It is preferable that metal have excellent corrosion resistance. When the conduit forming unit is used in the ventricular assist system, it is also preferable that metal also have excellent compatibility with a living tissue. From such a viewpoint, as metal, for example, titanium can be exemplified.

[5] In the conduit forming unit according to the present invention, it is preferable that the first connection tubular body, the cylindrical tubular body and the second connection tubular body be formed such that, in a state where the first connection tubular body, the cylindrical tubular body and the second connection tubular body are connected to each other, an inner peripheral surface of the first connection tubular body, an inner peripheral surface of the cylindrical tubular body, and an inner peripheral surface of the second connection tubular body form a non-stepped surface in an axial direction.

In this manner, the inner peripheral surface of the first connection tubular body, the inner peripheral surface of the cylindrical tubular body, and the inner peripheral surface of the second connection tubular body form the non-stepped surface in the axial direction and hence, it is possible to allow a fluid to flow through the first connection tubular body, the cylindrical tubular body, and the second connection tubular body without stagnation. In this specification, "non-stepped surface" means a surface on which steps do not substantially exist.

[6] In the conduit forming unit according to the present invention, it is preferable that an annular sealing member be interposed between the first connection tubular body and the cylindrical tubular body, and an annular sealing member be interposed between the second connection tubular body and the cylindrical tubular body.

With such a configuration, the first connection tubular body and the cylindrical tubular body can be connected to each other in a liquid tight state, and the second connection tubular body and the cylindrical tubular body can be connected to each other in a liquid tight state.

[7] In the conduit forming unit according to the present invention, it is preferable that, in the plurality of pawl portions of the cylindrical pawl equipped nut, a surface of each of the pawl portions which faces either of the flanges be a tapered surface inclined inward as the surface extends toward a center of the cylindrical pawl equipped nut in a radial direction.

In this manner, the surface of each pawl portion which faces the flange is the tapered surface inclined inward as the surface extends toward the center of the cylindrical pawl equipped nut. Accordingly, in making the plurality of pawl portions of the cylindrical pawl equipped nut engage with the flange by making the plurality of pawl portions get over the flange of the cylindrical tubular body, the plurality of pawl portions can easily get over the flange and hence, the cylindrical pawl equipped nut can be easily mounted on the cylindrical tubular body.

[8] In the conduit forming unit according to the present invention, it is preferable that recessed grooves be formed on respective outer peripheral surfaces of the plurality of protruding lugs in a circumferential direction, and a projection which engages with the recessed grooves be formed on an inner peripheral surface of the retaining ring.

In this manner, the recessed grooves are formed on the respective outer peripheral surfaces of the plurality of protruding lugs in the circumferential direction, and the projection which engages with the recessed grooves is formed on the inner peripheral surface of the retaining ring. Accordingly, in annularly mounting the retaining ring on the protruding lugs of the cylindrical pawl equipped nut, it is sufficient to make the retaining ring slide on the cylindrical pawl equipped nut and to make the projection of the retaining ring engage with the recessed grooves formed on the protruding lugs of the cylindrical pawl equipped nut.

[9] A tube joint according to the present invention is a tube joint configured to be used for connecting: a cylindrical tubular body where flanges are respectively formed on an outer peripheral surface of a first end portion of the cylindrical tubular body and an outer peripheral surface of a second end portion of the cylindrical tubular body on a side opposite to the first end portion in an axial direction of a tubular body, the flanges being integrally formed on the tubular body in a protruding manner toward an outer side in a radial direction; and a first connection tubular body disposed on a first end portion side of the cylindrical tubular body, and having male threads on an outer peripheral surface of the first connection tubular body. The tube joint is also configured to be used for connecting: the cylindrical tubular body; and a second connection tubular body disposed on a second end portion side of the cylindrical tubular body, and having male threads on an outer peripheral surface of the second connection tubular body. The tube joint includes: a cylindrical pawl equipped nut where female threads which are threadedly engageable with the male threads formed on the first connection tubular body or the male threads formed on the second connection tubular body are formed on an inner peripheral surface of the cylindrical pawl equipped nut, a plurality of pawl portions which are engageable with either of the flanges of the cylindrical tubular body are formed in the cylindrical pawl equipped nut in a circumferential direction and in a protruding manner toward an inside in a radial direction, the plurality of pawl portions are configured to get over the either of the flanges of the cylindrical tubular body and engage with the either of the flanges, and the female threads are configured to threadedly engage with the male threads of the first connection tubular body or the male threads of the second connection tubular body so as to bring about a fastening state of the cylindrical pawl equipped nut thus enabling connection between the first connection tubular body and the cylindrical tubular body or connection between the second connection tubular body and the cylindrical tubular body; and a retaining ring being annularly mountable on an outer peripheral surface of the pawl equipped nut, the retaining ring being capable of retaining engagement of the plurality of pawl portions with the either of the flanges of the cylindrical tubular body, wherein the plurality of pawl portions of the pawl quipped nut are each formed on each of distal end portions of a plurality of protruding lugs formed on the pawl equipped nut in a protruding manner in an axial direction at a predetermined interval in a circumferential direction, and the plurality of protruding lugs have elasticity in a radial direction, and the retaining ring is annularly mounted on the plurality of protruding lugs, and the retaining ring is configured to impart a pressing force to the plurality of pawl portions in a radial direction in a state where the retaining ring is annularly mounted on the plurality of protruding lugs.

The tube joint according to the present invention can be used as the tube joint in the conduit forming unit described in any one of [1] to [8] described above. That is, the tube joint according to the present invention is formed of the tube joint which can be used for connecting the cylindrical tubular body where the flanges are respectively formed on one end portion and the other end portion of the cylindrical tubular body and the first connection tubular body disposed on the first end portion side of the cylindrical tubular body to each other, and the tube joint which can be used for connecting the cylindrical tubular body and the second connection tubular body disposed on the second end portion side of the cylindrical tubular body to each other.

According to the tube joint of the present invention, in connecting the first connection tubular body and the cylindrical tubular body to each other, the first connection tubular body and the cylindrical tubular body can be connected to each other such that a rotational force about an axis is not applied to the first connection tubular body, and a rotational force about an axis is also not applied to the cylindrical tubular body. In the same manner, also in connecting the second connection tubular body and the cylindrical tubular body to each other, the second connection tubular body and the cylindrical tubular body can be connected to each other such that a rotational force about an axis is not applied to the second connection tubular body, and a rotational force about an axis is also not applied to the cylindrical tubular body.

For example, the case where the first connection tubular body and the cylindrical tubular body are connected to each other is described as an example. The first connection tubular body is pressed by a hand or the like in a state where the cylindrical pawl equipped nut engages with the flange of the cylindrical tubular body. In such a state, the cylindrical pawl equipped nut which is in engagement with the flange of the cylindrical tubular body is made to slide toward a rear side along an outer peripheral surface of the first connection tubular body so that the female threads of the cylindrical pawl equipped nut threadedly engage with the male threads of the first connection tubular body whereby the cylindrical pawl equipped nut can be fastened. In performing such an operation, a fastening operation of the cylindrical pawl equipped nut can be performed without moving the first connection tubular body and the cylindrical tubular body. This is because the cylindrical pawl equipped nut is not stopped with respect to the cylindrical tubular body by thread engagement but is simply configured such that the pawl portions are made to engage with the flange. The same operation is performed in connecting the second connection tubular body and the cylindrical tubular body to each other.

Also in the tube joint according to the present invention, it is preferable that the tube joint have substantially the same technical features as the conduit forming unit described in any one of the [2] to [8].

DESCRIPTION OF EMBODIMENTS

Hereinafter, an embodiment of the present invention is described.

Figure 1:
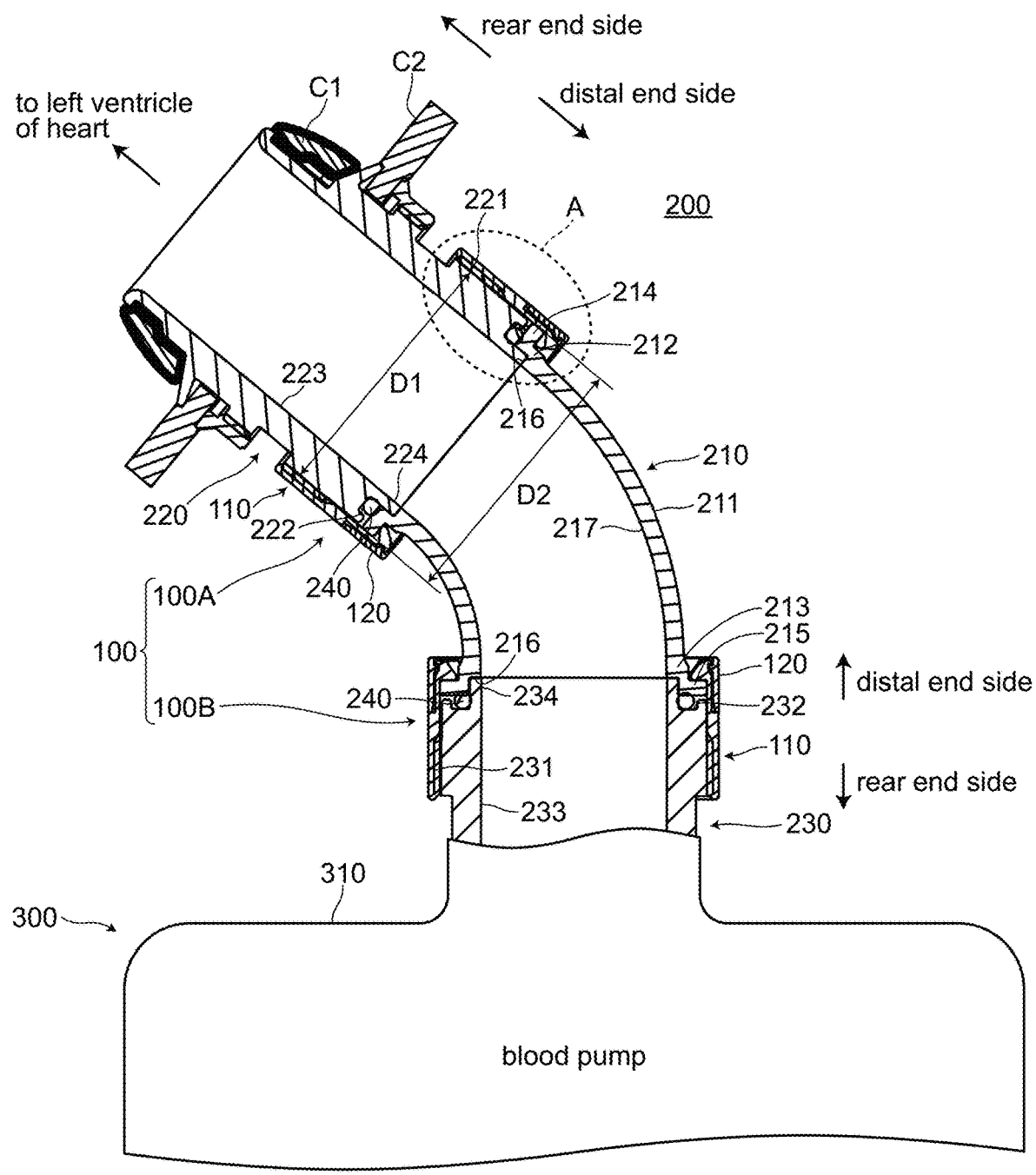
FIG. 1 is a cross-sectional view of a conduit forming unit 200 according to an embodiment taken along an axial direction.

FIG. 1 is a cross-sectional view of a conduit forming unit 200 according to the embodiment taken along an axial direction.

Figure 2:
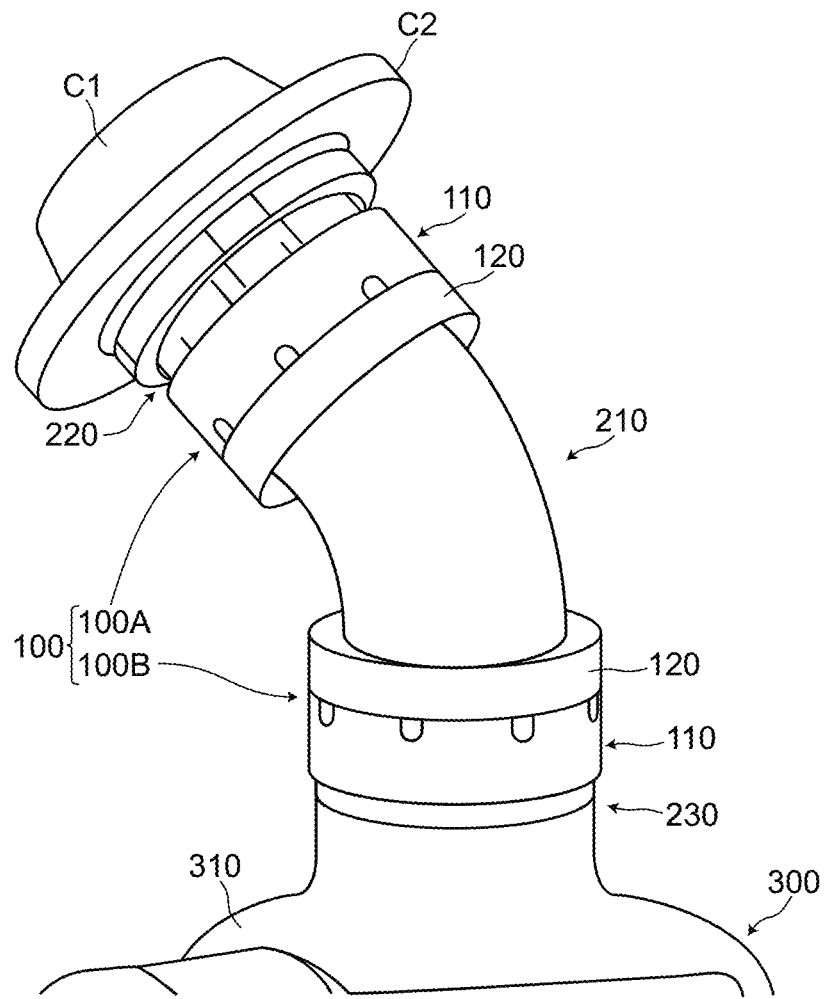
FIG. 2 is an external appearance perspective view of the conduit forming unit 200 according to the embodiment shown in FIG. 1.

FIG. 2 is an external appearance perspective view of the conduit forming unit 200 according to the embodiment shown in FIG. 1.

Figure 3:
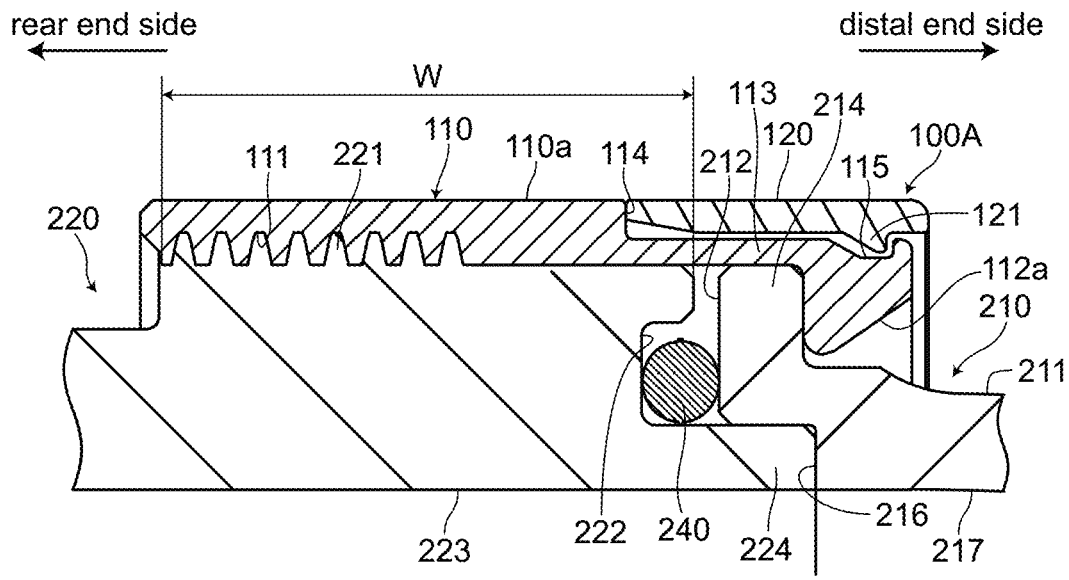
FIG. 3 is an enlarged view showing a portion of the conduit forming unit 200 in a frame A indicated by a broken line in FIG. 1 in an enlarged manner.

FIG. 3 is an enlarged view showing a portion of the conduit forming unit 200 in a frame A indicated by a broken line in FIG. 1 in an enlarged manner.

First, the overall configuration of the conduit forming unit 200 according to the embodiment is described and, thereafter, tube joints 100 used in the conduit forming unit 200 according to the embodiment is described.

As shown in FIG. 1 to FIG. 3, the conduit forming unit 200 according to the embodiment includes: a cylindrical tubular body 210 where flanges 214, 215 are respectively formed on an outer peripheral surface of a first end portion 212 and an outer peripheral surface of a second end portion 213 on a side opposite to the first end portion 212 in an axial direction of a tubular body 211, the flanges are integrally formed on the tubular body 211 in a protruding manner toward an outer side in a radial direction; a first connection tubular body 220 disposed coaxially with the cylindrical tubular body 210 on a first end portion 212 side of the cylindrical tubular body 210, and having male threads 221 (see the detail of the male threads 221 in FIG. 3) on an outer peripheral surface; a second connection tubular body 230 disposed coaxially with the cylindrical tubular body 210 on a second end portion 213 side of the cylindrical tubular body 210, and having male threads 231 on an outer peripheral surface; a tube joint 100 which connects the first end portion 212 of the cylindrical tubular body 210 and the first connection tubular body 220 to each other (referred to as a tube joint 100A); and a tube joint 100 which connects the second end portion 212 of the cylindrical tubular body 210 and the second connection tubular body 230 to each other (referred to as a tube joint 100B).

FIG. 3 which is an enlarged view is a view showing a portion (the portion in a frame A indicated by a broken line in FIG. 1) of the first connection tubular body 220 in an enlarged manner. On the other hand, an enlarged view is not provided for the corresponding portion (the portion corresponding to the portion in the frame A indicated by a broken line in FIG. 1) of the second connection tubular body 230. However, the corresponding portion (the portion corresponding to the portion in the frame A indicated by a broken line in FIG. 1) of the second connection tubular body 230 has substantially the same configuration as the configuration shown in FIG. 3. In the second connection tubular body 230, the configuration of the portion corresponding to the portion in the frame A indicated by a broken line in FIG. 1 is opposite to the configuration shown in FIG. 3 in the lateral arrangement.

Hereinafter, "a cylindrical tubular body 210 where flanges 214, 215 are respectively formed on an outer peripheral surface of a first end portion 212 and an outer peripheral surface of a second end portion 213 on a side opposite to the first end portion 212 in an axial direction of a tubular body 211, the flanges are integrally formed on the tubular body 211 in a protruding manner toward an outer side in a radial direction" may be also abbreviated as "cylindrical tubular body 210 having a flange on each of both end portions".

The tube joint 100A which connects the first end portion 212 of the cylindrical tubular body 210 and the first connection tubular body 220 to each other, and the tube joint 100B which connects the second end portion 213 of the cylindrical tubular body 210 and the second connection tubular body 230 to each other have the same configuration. Accordingly, these tube joint 100A and tube joint 100B can be used at the time of connecting the first connection tubular body 220 and the cylindrical tubular body 210 to each other as well as at the time of connecting the second connection tubular body 230 and the cylindrical tubular body 210 to each other. The detailed configurations of the tube joint 100A and the tube joint 100B are described later. Further, in describing the configurations of the tube joint 100A and the tube joint 100B, there may be a case where the tube joint 100A and the tube joint 100B are collectively described as "tube joint 100".

Figure 7:
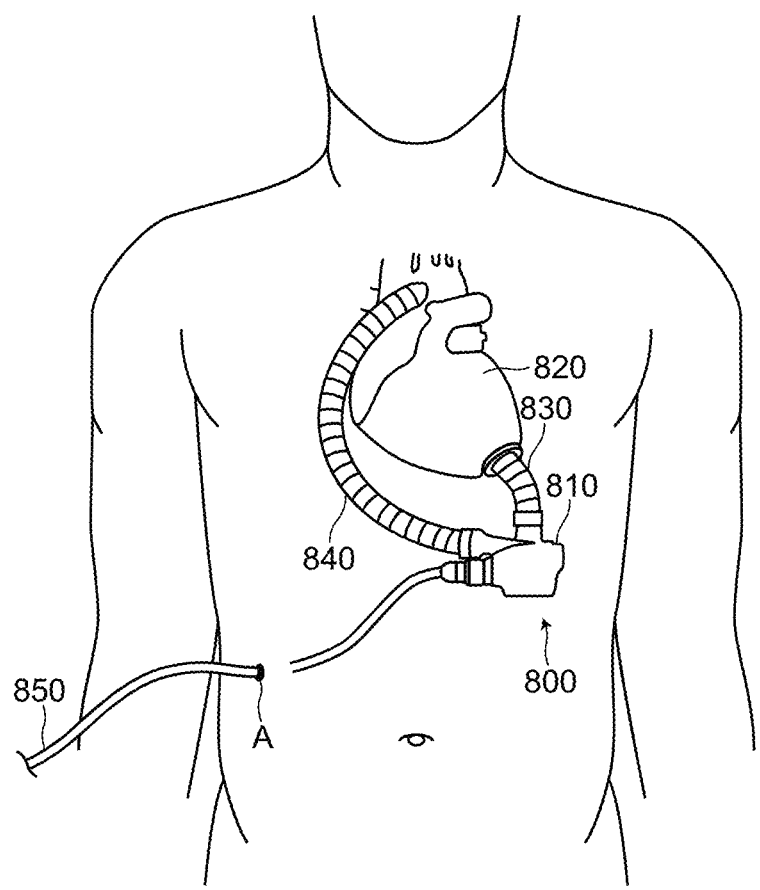
FIG. 7 is a view for describing a ventricular assist system 800 described in patent literature 1.
Figure 8:
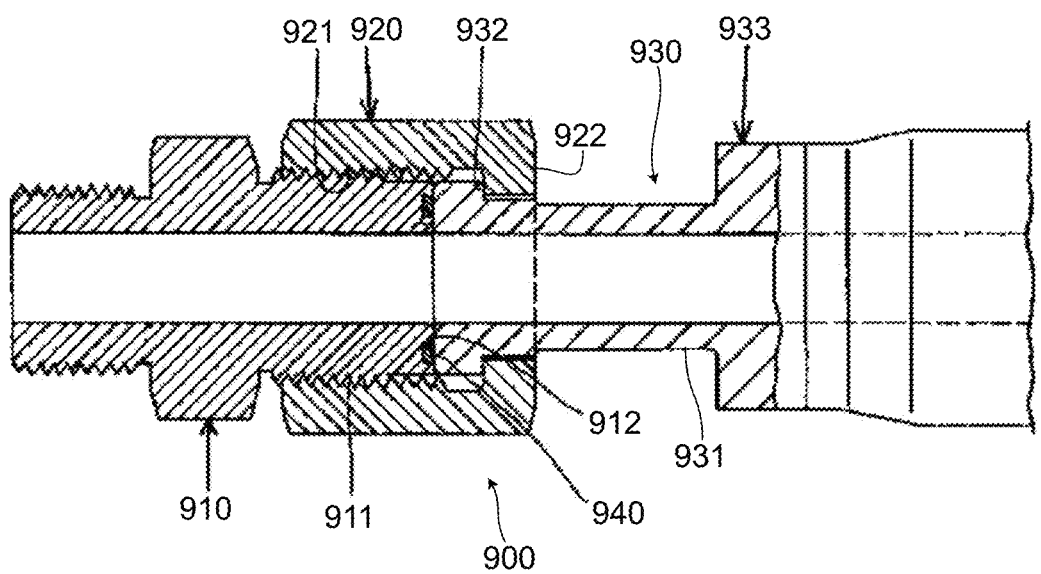
FIG. 8 is a view for describing a tube joint 900 described in patent literature 2.

The conduit forming unit 200 according to the embodiment can be used between the heart 820 and the blood pump 810 in the ventricular assist system 800 shown in FIG. 7, for example. In this case, the cylindrical tubular body 210 in the conduit forming unit 200 according to the embodiment corresponds to the artificial blood vessel (inflow side artificial blood vessel) 830 shown in FIG. 7.

The first connection tubular body 220 has a function of a cannula connected to a left ventricle of a heart, and has a function of guiding blood flowing out from the heart to the cylindrical tubular body 210. The cannula used in this embodiment has two cuffs, that is, a first cuff C1 and a second cuff C2. However, the cannula is not limited to a cannula having two cuffs, and the cannula may be a cannula which has one cuff.

On the other hand, the second connection tubular body 230 is connected to a blood pump 300, and has a function of allowing blood which flows from the first connection tubular body 220 through the cylindrical tubular body 210 to flow into the blood pump 300. In this embodiment, assume that the second connection tubular body 230 is integrally formed with a body of the blood pump 300 (referred to as a blood pump body 310) in a protruding manner.

In describing the first connection tubular body 220 and the second connection tubular body 230, respective sides of the first connection tubular body 220 and the second connection tubular body 230 directed toward the cylindrical tubular body 210 are assumed as distal end sides, and respective sides of the first connection tubular body 220 and the second connection tubular body 230 opposite to the distal end sides are assumed as rear end sides. End portions of the first connection tubular body 220 and the second connection tubular body 230 positioned on the distal end sides are assumed as distal end portions, and end portions of the first connection tubular body 220 and the second connection tubular body 230 positioned on the rear end sides are assumed as rear end portions.

The cylindrical tubular body 210, the first connection tubular body 220 and the second connection tubular body 230 are made of a material (metal) which is a non-flexible rigid member having excellent rigidity and excellent corrosion resistance, and also having excellent compatibility with a living tissue. As metal, for example, titanium or the like can be preferably used. Further, the cylindrical tubular body 210 is a so-called "bent tube" where the tube body 211 is gently bent in an axial direction.

The cylindrical tubular body 210, the first connection tubular body 220 and the second connection tubular body 230 each have the same inner diameter. In a state where the first connection tubular body 220 and the cylindrical tubular body 210 are connected to each other and the second connection tubular body 230 and the cylindrical tubular body 210 are connected to each other, respective inner peripheral surfaces of the first connection tubular body 220, the cylindrical tubular body 210 and the second connection tubular body 230 form a non-stepped surface (a surface on which steps do not substantially exist) in an axial direction.

A region W from the distal end portion of the first connection tubular body 220 to a portion of the first connection tubular body 220 within which the male threads 221 are formed is set as a connection region W (see FIG. 3), and an outer diameter D1 (see FIG. 1) of the first connection tubular body 220 in the connection region W is set equal to an outer diameter D2 (see FIG. 1) of the flange 214 of the cylindrical tubular body 210. The same configuration is adopted on a second connection tubular body 230 side. Accordingly, a tube wall thickness of the first connection tubular body 220 in the connection region W and a tube wall thickness of the second connection tubular body 230 in the connection region W are set larger than a wall thickness of the tubular body 211 of the cylindrical tubular body 210.

In this manner, by setting the outer diameter D1 of the first connection tubular body 220 and the second connection tubular body 230 in the respective connection regions W equal to the outer diameter D2 of the flange 214 of the cylindrical tubular body 210, in a state where the first connection tubular body 220 and the second connection tubular body 230 are each connected to the cylindrical tubular body 210, the outer peripheral surfaces of the first connection tubular body 220 and the second connection tubular body 230 in the respective connection regions W become coplanar with the outer peripheral surfaces of the flanges 214, 215 of the cylindrical tubular body 210 forming no stepped portions.

On the distal end portion of the first connection tubular body 220, a sealing member mounting groove 222 for mounting an annular sealing member 240 (see the detail of the sealing member mounting groove 222 in FIG. 3) is formed. Various sealing members can be used as the sealing member 240. In this embodiment, an O-ring having a circular cross section is used. The O-ring is made of a material which has liquid tightness and is elastically deformed when the material receives an external pressure. On an inner peripheral surface 223 side of the distal end portion of the first connection tubular body 220, the protruding portion 224 which protrudes further toward the distal end side from the distal end portion is formed in a circumferential direction.

In the same manner, also with respect to the second connection tubular body 230, a seal member mounting groove 232 for mounting a sealing member (O-ring) is formed on the distal end portion of the second connection tubular body 230. Also on an inner peripheral surface 233 side of the distal end portion of the second connection tubular body 230, a protruding portion 234 further protruding toward the distal end side from the distal end portion is formed in the circumferential direction.

On the other hand, on the first end portion 212 and the second end portion 213 of the cylindrical tubular body 210, recessed portions 216 which receive the protruding portion 224 of the first connection tubular body 220 and the protruding portion 234 of the second connection tubular body 230 are respectively formed in the circumferential direction. With such a configuration, when the first connection tubular body 220 and the cylindrical tubular body 210 are brought into a connection state, the protruding portion 224 of the first connection tubular body 220 and the recessed portion 216 of the cylindrical tubular body 210 are brought into a matching state. In the same manner, when the second connection tubular body 230 and the cylindrical tubular body 210 are brought into a connection state, the protruding portion 234 of the second connection tubular body 230 and the recessed portion 216 of the cylindrical tubular body 210 are brought into a matching state. In such a state, the sealing member 240 is interposed between the first connection tubular body 220 and the cylindrical tubular body 210, and the sealing member 240 is interposed between the second connection tubular body 230 and the cylindrical tubular body 210.

Subsequently, the tube joint 100 (tube joints 100A, 100B) which is used in the conduit forming unit 200 according to the embodiment is described in detail with reference to FIG. 4, FIG. 5A and FIG. 5B in addition to FIG. 1 to FIG. 3. Also in describing the respective constitutional elements which constitute the tube joint 100, sides of the respective constitutional elements which constitute the tube joint 100 directed toward the cylindrical tubular body 210 are assumed as distal end sides, and sides opposite to the distal end sides are assumed as rear end sides. End portions of the respective constitutional elements of the tube joint 100 positioned on the distal end side are assumed as distal end portions, and end portions of the respective constitutional elements of the tube joint 100 positioned on the rear end side are assumed as rear end portions. The tube joint 100 includes, as constitutional elements thereof, a cylindrical pawl equipped nut 110 and a retaining ring 120.

Figure 4:
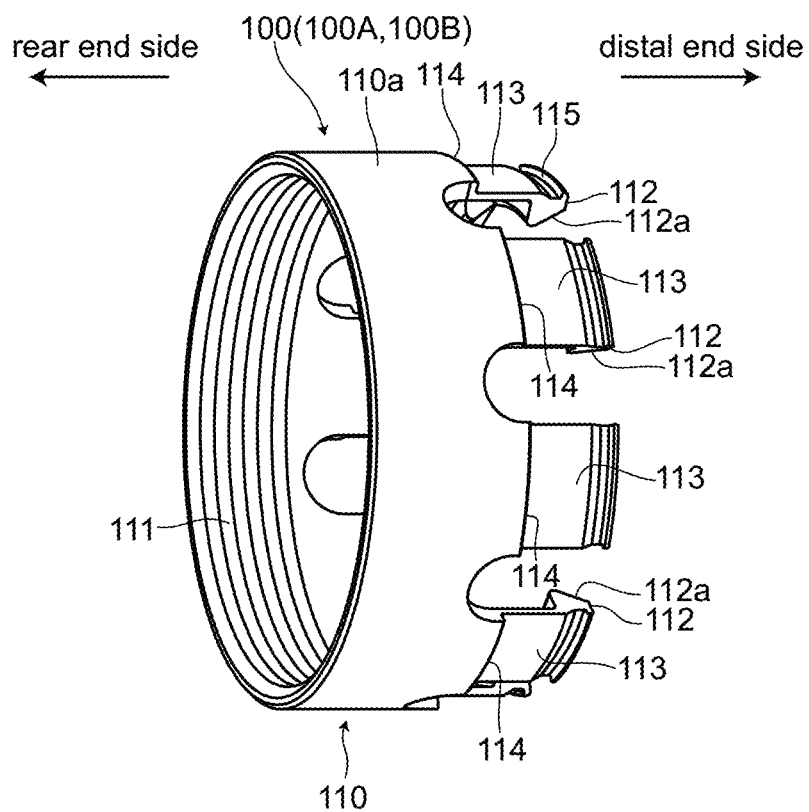
FIG. 4 is a perspective view showing a cylindrical pawl equipped nut 110 which is one of constitutional elements of a tube joint 100.

FIG. 4 is a perspective view showing the cylindrical pawl equipped nut 110 which is one of the constitutional elements of the tube joint 100. The cylindrical pawl equipped nut 110 is described with reference to FIG. 4 and also with reference to FIG. 1 to FIG. 3 described previously. The cylindrical pawl equipped nut 110 having the same configuration is used in each of the tube joint 100A and the tube joint 100B. Hereinafter, the cylindrical pawl equipped nut 110 may be also abbreviated as "pawl equipped nut 110" by omitting "cylindrical".

With respect to the pawl equipped nut 110, as shown in FIG. 4, female threads 111 which are threadedly engageable with the male threads 221 formed on the first connection tubular body 220 or the male threads 231 formed on the second connection tubular body 230 are formed on an inner peripheral surface of the pawl equipped nut 110. The female threads 111 are formed on the inner peripheral surface within a predetermined range on the rear end side.

A plurality of pawl portions 112 which are engageable with the flange 214, 215 of the cylindrical tubular body 210 are formed in the pawl equipped nut 110 in the circumferential direction and in a protruding manner toward the inside in the radial direction. The plurality of pawl portions 112 are each formed on each of distal end portions of a plurality of protruding lugs 113 formed on a body portion 110a of the pawl equipped nut 110 in a protruding manner in an axial direction at a predetermined interval in the circumferential direction. The plurality of these pawl portions 112 are formed such that the protruding lugs 113 have elasticity in the radial direction and hence, the pawl portions 112 are expandable and shrinkable in the radial direction. "The plurality of pawl portions 112" may be also expressed as "respective pawl portions 112".

By allowing the pawl equipped nut 110 to have such a configuration, the respective pawl portions 112 engage with the flange 214, 215 by getting over the flange 214, 215 of the cylindrical tubular body 210. That is, the protruding lugs 113 have elasticity and hence, it is possible to allow the respective pawl portions 112 to get over the flange 214, 215 of the cylindrical tubular body 210 in a state where the respective pawl portions 112 are expanded in the radial direction, and when the respective pawl portions 112 have gotten over the flange 214, 215, the respective pawl portions 112 substantially return to an original state (state before the respective pawl portions 112 are expanded in the radial direction). Accordingly, the respective pawl portions 112 engage with the flange 214, 215 in a state where the respective pawl portions 112 have completed getting over the flange 214, 215 of the cylindrical tubular body 210.

With respect to each pawl portion 112 of the pawl equipped nut 110, an outer surface (a surface directed toward the distal end side) of each pawl portion 112 is a tapered surface 112a inclined inward (toward the rear end side in an axial direction) as the outer surface extends toward the center of the pawl equipped nut 110 in the radial direction. With such a configuration, each pawl portion 112 can easily get over the flange 214, 215 in making the pawl equipped nut 110 engage with the flange 214, 215.

Each of the protruding lugs 113 of the pawl equipped nut 110 is formed in a thin plate shape having a small thickness compared to the body portion 110a of the pawl equipped nut 110 and hence, stepped portions 114 are formed between the protruding lugs 113 and the body portion 110a of the pawl equipped nut 110.

The protruding lugs 113 of the pawl equipped nut 110 also form an annular mounting region when the retaining ring 120 described later is annularly mounted on the pawl equipped nut 110. Recessed grooves 115 with which a projection 121 (see FIG. 5A and FIG. 5B) formed on an inner peripheral surface of the retaining ring 120 engage are formed on outer peripheral surfaces of the protruding lugs 113 of the pawl equipped nut 110 in the circumferential direction. A height of the stepped portions 114 formed between the protruding lugs 113 and the body portion 110a of the pawl equipped nut 110 corresponds to a wall thickness of the retaining ring 120. Accordingly, in a state where the retaining ring 120 is annularly mounted on the protruding lugs 113 of the pawl equipped nut 110, it is possible to make an outer peripheral surface of the body portion 110a of the pawl equipped nut 110 and the outer peripheral surface of the retaining ring 120 coplanar forming no stepped portion between these outer peripheral surfaces (see FIG. 2).

Next, the retaining ring 120 is described.

Figure 5A:
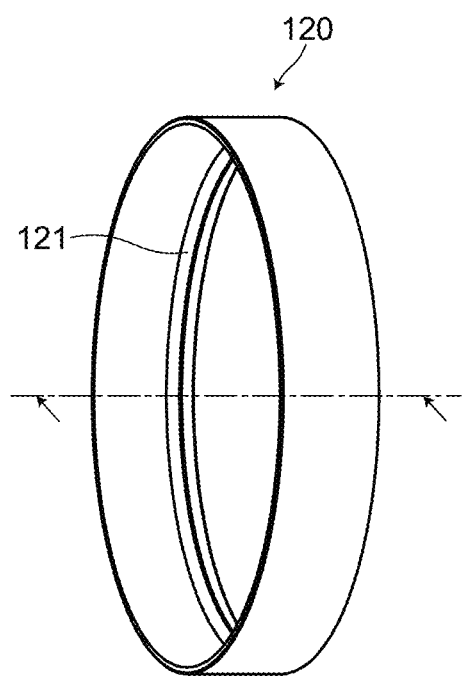
FIG. 5A and FIG. 5B are views showing a retaining ring 120 which is one of the constitutional elements of the tube joint 100.
Figure 5B:
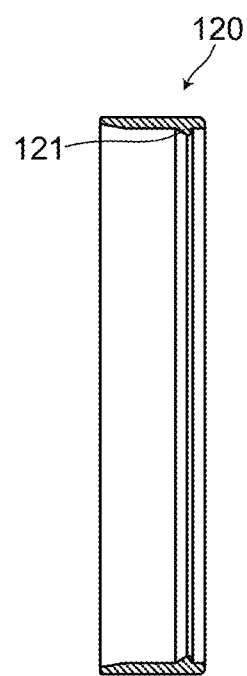

FIG. 5A and FIG. 5B are views showing the retaining ring 120 which is one of the constitutional elements of the tube joint 100. FIG. 5A is a perspective view of the retaining ring 120. FIG. 5B is a cross-sectional view obtained by cutting the retaining ring 120 shown in FIG. 5A in halves along an axial direction. In the same manner as the cylindrical pawl equipped nut 110, the retaining ring 120 also has the same configuration in the tube joint 100A and the tube joint 100B.

The retaining ring 120 has a function of retaining engagement of the respective pawl portions 112 in a state where the respective pawl portions 112 of the pawl equipped nut 110 engage with the flange 214, 215 of the cylindrical tubular body 210. As shown in FIG. 5A and FIG. 5B, the retaining ring 120 is formed in a cylindrical shape and having an opening at both ends. The projection 121 which engages with the recessed grooves 115 formed on the protruding lugs 113 of the pawl equipped nut 110 is formed on the inner peripheral surface of the retaining ring 120. An inner diameter of the retaining ring 120 is sufficiently larger than an outer diameter of the flange 214, 215 of the cylindrical tubular body 210. That is, the retaining ring 120 has the inner diameter of a size which allows the flange 214, 215 of the cylindrical tubular body 210 to easily pass through the retaining ring 120.

With respect to the retaining ring 120 having such a configuration, in annularly mounting the retaining ring 120 on the protruding lugs 113 of the pawl equipped nut 110, it is sufficient to make the retaining ring 120 slide on the pawl equipped nut 110, and to make the projection 121 of the retaining ring 120 engage with the recessed grooves 115 formed on the protruding lugs 113 of the pawl equipped nut 110. By making the projection 121 of the retaining ring 120 engage with the recessed grooves 115 formed on the protruding lugs 113 of the pawl equipped nut 110, the engagement of the plurality of pawl portions with the flange of the cylindrical tubular body can be retained. Specific steps of annularly mounting the retaining ring 120 on the protruding lugs 113 of the pawl equipped nut 110 are described with reference to FIG. 6A to FIG. 6E.

The tube joint 100 has been described above. With the use of the tube joint 100 having such a configuration, the first connection tubular body 230 and the cylindrical tubular body 210 can be connected to each other, and the second connection tubular body 220 and the cylindrical tubular body 210 can be connected to each other. That is, with the use of the tube joint 100A, the first connection tubular body 220 and the cylindrical tubular body 210 can be connected to each other. With the use of the tube joint 100B having the same configuration as the joint 100A, the second connection tubular body 230 and the cylindrical tubular body 210 can be connected to each other.

Subsequently, connection steps of connecting the cylindrical tubular body 210 and the first connection tubular body 220 and the second connection tubular body 230 to each other are described. Here, the steps of connecting the cylindrical tubular body 210 and the first connection tubular body 220 to each other using the tube joint 100A are described. In this embodiment, the first connection tubular body 220 has a function of a cannula, and an end portion (rear end portion) of the first connection tubular body 220 on which the first cuff C1 and the second cuff C2 are mounted is connected to the left ventricle of the heart.

In this embodiment, the case where the cannula has two cuffs, that is, the first cuff C1 and the second cuff C2 is exemplified. In this case, the first cuff is sutured to the inside of the heart, and the second cuff C2 is sutured to a surface of the heart. Here, the connection steps are described with reference to FIG. 6A to FIG. 6E with respect to a case where the first connection tubular body 220 is in a state where the first connection tubular body 220 is already connected to the heart, and the first connection tubular body 220 in a state where the first connection tubular body 220 is connected to the heart and the cylindrical tubular body 210 are connected to each other using the tube joint 100A. In FIG. 6A to FIG. 6E, a state or a mode where the first connection tubular body 220 is connected to the heart is not shown.

FIG. 6A to FIG. 6E are views for describing connection steps of connecting the first connection tubular body 220 and the cylindrical tubular body 210 to each other using the tube joint 100A. In FIG. 6A to FIG. 6E, in describing the connection steps, symbols which are not necessary for the description are not shown in the drawing.

Figure 6A:
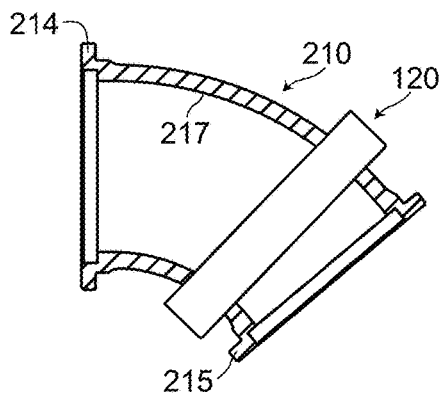
FIG. 6A to FIG. 6E are views for describing connection steps of connecting a first connection tubular body 220 and a cylindrical tubular body 210 to each other using a tube joint 100A.

First, the retaining ring 120 is annularly mounted on the cylindrical tubular body 210 (see FIG. 6A). The retaining ring 120 has the inner diameter of a size which allows the flange 214 of the cylindrical tubular body 210 to easily pass through the retaining ring 120. With such a configuration, as shown in FIG. 6A, the retaining ring 120 can be annularly mounted on the cylindrical tubular body 210. In this manner, as the first step, the retaining ring 120 is annularly mounted on the cylindrical tubular body 210. In this state, the retaining ring 120 is freely movable on the outer peripheral surface of the cylindrical tubular body 210.

Next, the pawl equipped nut 110 is made to engage with the flange 214 of the cylindrical tubular body 210. In this case, the respective pawl portions 112 of the pawl equipped nut 110 are expanded in the radial direction, and are made to get over the flange 214 of the cylindrical tubular body 210, and the respective pawl portions 112 are made to engage with the flange 214 (see FIG. 6B). In such a state, the pawl equipped nut 110 can be freely rotated (idling) on the cylindrical tubular body 210 in a circumferential direction of the flange 214, and the pawl equipped nut 110 can be made to slide toward the distal end side (a right direction in FIG. 6A to FIG. 6E) along an axial direction of the cylindrical tubular body 210.

Next, the retaining ring 120 is annularly mounted on the pawl equipped nut 110. In annularly mounting the retaining ring 120 on the pawl equipped nut 110, the pawl equipped nut 11 is made to slightly slide toward the distal end side (the right direction in FIG. 6A to FIG. 6E), and is positioned such that the protruding lugs 113 of the pawl equipped nut protrude from the flange 214 of the cylindrical tubular body 210 toward the distal end side (the right direction in FIG. 6A to FIG. 6E) (see FIG. 6C). By positioning the protruding lugs 113 of the pawl equipped nut 110 as shown in FIG. 6C, the protruding lugs 113 are no more supported by the flange 214 and hence, the protruding lugs 113 have elasticity in the radial direction.

Figure 6B:
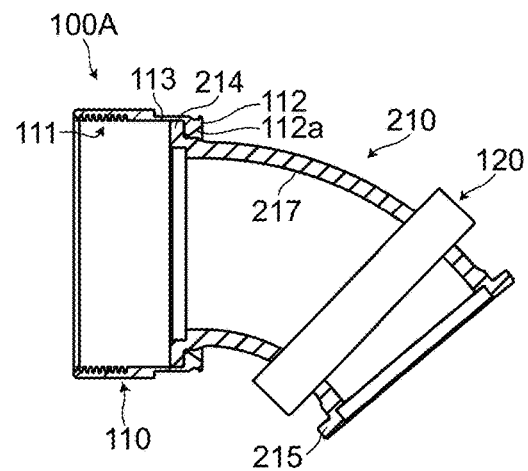
Figure 6C:
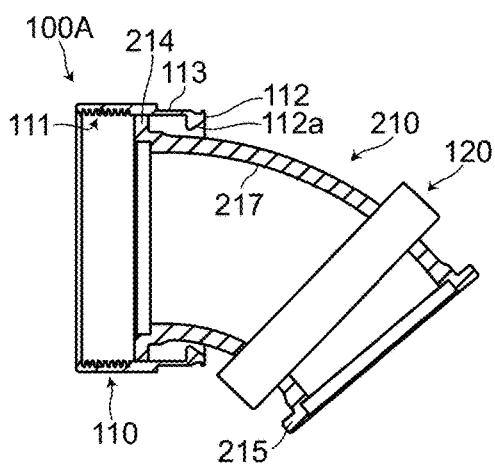
Figure 6D:
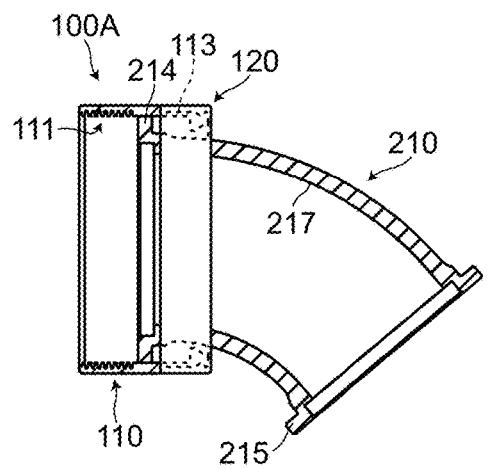

In a state where the protruding lugs 113 of the pawl equipped nut 110 are positioned as shown in FIG. 6C, the retaining ring 120 is annularly mounted on the pawl equipped nut 110. In annularly mounting the retaining ring 120 on the pawl equipped nut 110, by making use of elasticity of the protruding lugs 113 of the pawl equipped nut 110, the retaining ring 120 is fitted on the pawl equipped nut 110 by slightly shrinking the protruding lugs 113 in the radial direction. With such an operation, the projection 121 formed on the retaining ring 120 engages with the recessed grooves 115 formed on the respective protruding lugs 113 of the pawl equipped nut 110 and hence, the retaining ring 120 can be annularly mounted on the pawl equipped nut 110 (see FIG. 6D).

In this manner, the retaining ring 120 is not annularly mounted on the pawl equipped nut 110 by fastening of threads. That is, the retaining ring 120 is annularly mounted on the pawl equipped nut 110 by performing an operation of making the retaining ring 120 slide on the outer peripheral surfaces of the protruding lugs 113 in the axial direction.

Next, the pawl equipped nut 110 in a state where the retaining ring 120 is annularly mounted on the pawl equipped nut 110 is mounted on the first connection tubular body 220. At this stage of the operation, as described previously, assume that the first connection tubular body 220 is already connected to the left ventricle of the heart.

In mounting the pawl equipped nut 110 on the first connection tubular body 220, the sealing member (O-ring) 240 is mounted in the sealing member mounting groove 222 formed on the first connection tubular body 220. Then, in a state where the first connection tubular body 220 is pressed by a hand or the like so as to prevent the movement of the first connection tubular body 220, the distal end portion of the first connection tubular body 220 is inserted into a rear end portion side of the pawl equipped nut 110, and the cylindrical pawl equipped nut 110 is made to slide toward a rear side along the outer peripheral surface of the first connection tubular body 220. Then, the pawl equipped nut 110 is fastened by rotating the pawl equipped nut 110 by making the female threads 111 of the pawl equipped nut 110 threadedly engage with the male threads of the first connection tubular body 220 in a state where the first connection tubular body 220 is pressed by a hand or the like so as to prevent the movement of the first connection tubular body 220.

At this state of the operation, the pawl equipped nut 110 is rotatable on the outer peripheral surface of the cylindrical tubular body 210. Accordingly, by pressing the cylindrical tubular body 210 by a hand or the like, the pawl equipped nut 110 can be fastened by rotating only the pawl equipped nut 110 without imparting a rotational force to the cylindrical tubular body 210.

By performing fastening of the pawl equipped nut 110 in this manner, the pawl equipped nut 110 further advances toward the rear end side (a left direction in FIG. 6A to FIG. 6E) of the first connection tubular body 220 while imparting a pressing force to the flange 214 toward the rear end side (the left direction in FIG. 6A to FIG. 6E). With such an operation, the flange 214 advances on the protruding portion 224 (see FIG. 3) of the first connection tubular body 220 in a sliding manner, and presses the sealing member (O-ring) 240. With such an operation, a state is obtained where the first connection tubular body 220 and the cylindrical tubular body 210 are brought into close contact with each other by way of the sealing member (O-ring) 240 (see FIG. 6E).

Figure 6E:
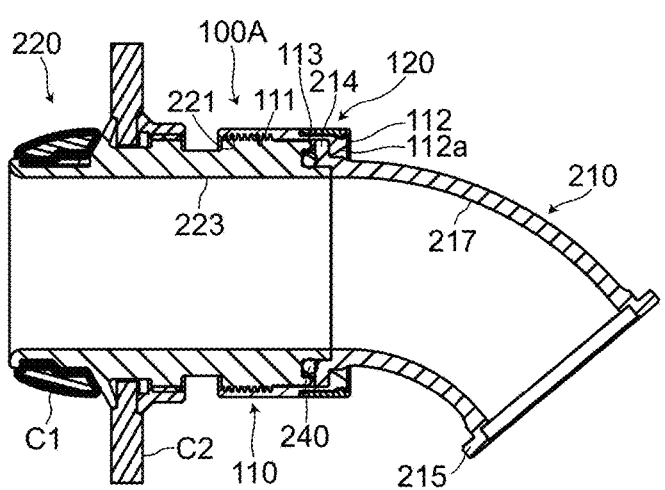

In a state shown in FIG. 6E, a state is brought about where the retaining ring 120 is annularly mounted on the pawl equipped nut 110. Accordingly, the retaining ring 120 imparts a pressing force in the radial direction to the respective pawl portions 112 of the pawl equipped nut 110 and hence, the engagement of the respective pawl portions 112 with the flange 214 can be retained.

That is, when the retaining ring 120 is not annularly mounted on the pawl equipped nut 110, there may be a case where a restoring force (a force which intends to expand the protruding lugs 113 in the radial direction) is generated in the protruding lugs 113 by elasticity of the protruding lugs 113. However, a state is obtained where the retaining ring 120 imparts a pressing force to the protruding lugs 113 so as to suppress the restoring force of the protruding lugs 113. Accordingly, the engagement of the respective pawl portions 112 with the flange 214 can be retained and hence, a state where the first connection tubular body 220 and the cylindrical tubular body 210 are brought into close contact with each other can be retained.

The protruding portion 224 (see FIG. 3) which protrudes toward the distal end side is formed on the distal end portion of the first connection tubular body 220, and the recessed portion 216 (see FIG. 3) which matches with the protruding portion 224 of the first connection tubular body is formed on the cylindrical tubular body 210. Accordingly, when the pawl equipped nut 110 presses the flange 214, the flange 214 slides on the protruding portion 224 of the first connection tubular body 220 and presses the sealing member (O-ring) 240 and hence, a state where the first connection tubular body 220 and the cylindrical tubular body 210 are brought into close contact with each other is further strengthened. Accordingly, it is possible to prevent with certainty a leakage of a fluid (blood from the heart in this case) flowing out from the first connection tubular body 220 to the cylindrical tubular body 210 to the outside.

Further, as shown in FIG. 6E, when a state is obtained where the first connection tubular body 220 and the cylindrical tubular body 210 are brought into close contact with each other, a stepped portion is eliminated between the inner peripheral surface 223 of the first connection tubular body 220 and the inner peripheral surface 217 of the cylindrical tubular body 210. Accordingly, the inner peripheral surface 223 of the first connection tubular body 220 and the inner peripheral surface 217 of the cylindrical tubular body 210 form a non-stepped surface (a surface on which steps do not substantially exist) in an axial direction. Accordingly, the flow of a fluid (blood from the heart) which flows out from the first connection tubular body 220 to the cylindrical tubular body 210 is not obstructed.

Although the case where the first connection tubular body 220 and the cylindrical tubular body 210 are connected to each other using the tube joint 100A has been described above, the second connection tubular body 230 and the cylindrical tubular body 210 can be connected to each other using the tube joint 100B having the same structure as the tube joint 100A. Connection steps of connecting the second connection tubular body 230 and the cylindrical tubular body 210 to each other using the tube joint 100B can be performed in the same manner as the case where the first connection tubular body 220 and the cylindrical tubular body 210 are connected to each other using the tube joint 100A and hence, the description of the connection steps is omitted.

As has been described above, the conduit forming unit 200 according to the embodiment shown in FIG. 1 can be constituted of: the cylindrical tubular body 210 having the flanges 214, 215 on both end portions (see FIG. 1 and FIG. 2); the first connection tubular body 220; and the second connection tubular body 230 having the same configuration as the first connection tubular body 220 (see FIG. 1 and FIG. 2); and the tube joint 100 (the tube joint 100A and the tube joint 100B). The conduit forming unit 200 according to the embodiment shown in FIG. 1 can be, as described above, used as the conduit forming unit disposed between the heart 820 and the blood pump 810 in the ventricular assist system 800 shown in FIG. 7.

By using the conduit forming unit 200 according to the embodiment as the conduit forming unit disposed between the heart 820 and the blood pump 810 in the ventricular assist system 800 shown in FIG. 7, the following various advantageous effects can be acquired.

First, the conduit forming unit 200 according to the embodiment uses the tube joint 100. Accordingly, in accordance with the connection steps shown in FIG. 6A to FIG. 6D, the first connection tubular body 220 and the cylindrical tubular body 210 having the flanges 214, 215 on both end portions can be connected to each other, and the cylindrical tubular body 210 and the second connection tubular body 230 can be connected to each other.

In connecting the cylindrical tubular body 210 to the first connection tubular body 220 in a state where the first connection tubular body 220 is connected to the heart, it is required that the first connection tubular body 220 and the cylindrical tubular body 210 can be connected to each other such that a rotational force about an axis is not applied to the first connection tubular body 220, and a rotational force about an axis is also not applied to the cylindrical tubular body 210. The conduit forming unit 200 according to the embodiment uses the tube joint 100 and hence, the conduit forming unit 200 can satisfy such requirement.

That is, the retaining ring 120 is annularly mounted on the cylindrical tubular body 210, and the pawl equipped nut 110 is made to engage with the flange 214 of the cylindrical tubular body 210 in advance (see FIG. 6A and FIG. 6B). Then, the retaining ring 120 is annularly mounted on the protruding lugs 113 of the pawl equipped nut (see FIG. 6D) in a state where the pawl equipped nut 110 is made to slide toward the distal end side (the right direction in FIG. 6A to FIG. 6E) (see FIG. 6C). In such an operation, the retaining ring 120 can be annularly mounted on the pawl equipped nut 110 by merely sliding the retaining ring 120 on the protruding lugs 113 of the pawl equipped nut toward the rear end side (the left direction in FIG. 6A to FIG. 6E)

Then, the pawl equipped nut 110 in a state where the retaining ring 120 is annularly mounted on the pawl equipped nut 110 is made to slide toward the rear end side along the outer peripheral surface of the first connection tubular body 220, and the pawl equipped nut 110 is fastened to the first connection tubular body 220 by making the female threads 111 of the pawl equipped nut 110 threadedly engage with the male thread 221 of the first connection tubular body 220 (see FIG. 6E). In performing such an operation, the fastening operation of the pawl equipped nut can be performed without moving the first connection tubular body 220 and the cylindrical tubular body 210. This is because the pawl equipped nut 110 is allowed to perform free rotation or idling with respect to the cylindrical tubular body 210.

Accordingly, in connecting the first connection tubular body 220 and the cylindrical tubular body 210 to each other, the first connection tubular body 220 and the cylindrical tubular body 210 can be connected to each other such that a rotational force about an axis is not applied to the first connection tubular body 220, and a rotational force about an axis is also not applied to the cylindrical tubular body 210. Particularly, the first connection tubular body 220 functions as a cannula, and the first cuff C1 and the second cuff C2 are connected to the left ventricle of the heart by suturing and hence, an excessively large force cannot be applied to the first connection tubular body 220. In a case where the cylindrical tubular body 210 is formed of a bent tube in a bent form, the position and the direction of an outlet (second end portion) of the cylindrical tubular body 210 can be determined based on the relationship between the position of the cylindrical tubular body 210 and the position of the blood pump 300.

In view of the above, in the case where the conduit forming unit 200 according to the embodiment is used in the ventricular assist system, it is required that the first connection tubular body 220 and the cylindrical tubular body 210 can be connected to each other such that a rotational force about an axis is not applied to the first connection tubular body 220, and a rotational force about an axis is also not applied to the cylindrical tubular body 210. The conduit forming unit according to the embodiment can satisfy such a requirement.

The substantially same operation is performed for connecting the second connection tubular body 230 and the cylindrical tubular body 210 to each other. The second connection tubular body 230 and the cylindrical tubular body 210 can be connected to each other such that a rotational force about an axis is not applied to the second connection tubular body 230, and a rotational force about an axis is not also applied to the cylindrical tubular body 210. Accordingly, when the second connection tubular body 230 is integrally formed with the blood pump 300, the second connection tubular body 230 mounted on the blood pump 300 and the cylindrical tubular body 210 can be connected to each other in a state where the position and the direction of the blood pump 300 are set at the appropriate position and in the appropriate direction.

According to the conduit forming unit 200 of the embodiment, the cylindrical tubular body 210, the first connection tubular body 220 and the second connection tubular body 230 are formed of a non-flexible rigid member (metal). In this embodiment, the rigid member is made of titanium. Accordingly, the cylindrical tubular body 210, the first connection tubular body 220 and the second connection tubular body 230 exhibit excellent rigidity and excellent corrosion resistance, exhibit excellent compatibility with a living tissue, and can prevent deformation such as twisting, collapsing and bending thus capable of supplying blood from the heart to the blood pump without stagnation.

The cylindrical tubular body 210 used in the conduit forming unit 200 according to the embodiment corresponds to an artificial blood vessel made of a flexible material used in a conventional ventricular assist system (for example, an artificial blood vessel using a material having flexibility such as ePTFE). By forming the artificial blood vessel using metal such as titanium, deformation such as twisting, collapsing and bending can be prevented with certainty. Particularly, in case of an artificial blood vessel which allows blood flowing out from a left ventricle of a heart to flow into a blood pump (inflow side artificial blood vessel), a negative pressure is liable to be generated in the artificial blood vessel. When the negative pressure is generated in the artificial blood vessel, there may be a case where a drawback such as collapsing occurs. However, by forming the artificial blood vessel using metal such as titanium, the occurrence of such a drawback can be prevented.

In the conduit forming unit 200 according to the embodiment, the respective inner peripheral surfaces of the first connection tubular body 220, the cylindrical tubular body 210 and the second connection tubular body 230 form a non-stepped surface (a surface on which steps do not substantially exist) in an axial direction. Accordingly, it is possible to allow blood flowing out from the heart to smoothly flow in these tubular bodies without stagnation. A projection such as a clip does not exist on respective outer peripheral surfaces of the first connection tubular body 220, the cylindrical tubular body 210 and the second connection tubular body 230 and hence, the respective outer peripheral surfaces become a substantially flat surface. Accordingly, these tubular bodies minimally affect other tissues in a living body.

The present invention is not limited to the above-mentioned embodiment, and various modifications can be carried out without departing from the gist of the present invention. For example, the following modifications can be also carried out.

(1) In the above-mentioned embodiment, in applying the conduit forming unit according to the present invention to the ventricular assist system, the case is particularly described where the conduit forming unit is used as the conduit forming unit disposed between the left ventricle of the heart to the blood pump. However, the present invention is not limited to such a case. For example, it is possible to use the conduit forming unit according to the present invention as a conduit forming unit disposed between the blood pump and an ascending aorta by changing a length and a shape of the cylindrical tubular body 210. The usage of the conduit forming unit according to the present invention is not limited to the ventricular assist system, and the conduit forming unit according to the present invention is applicable to various usages.

(2) In the above-mentioned embodiment, the case is exemplified where the conduit forming unit according to the present invention is used in the ventricular assist system. Accordingly, in the above-mentioned embodiment, in view of the positional relationship between the heart and the blood pump, the cylindrical tubular body is formed of a bent tube which is in a bent form. On the other hand, in a case where the conduit forming unit according to the present invention is used in locations other than the ventricular assist system, it is not always necessary that the cylindrical tubular body is not in a bent form. The cylindrical tubular body may be a cylindrical tubular body having various shapes such as a straight-line shape, an S shape, a U shape and the like corresponding to usages.

(3) In the above-mentioned embodiment, the case is exemplified where titanium is used as a material for forming the first connection tubular body, the cylindrical tubular body and the second connection tubular body. However, other metals can be also used provided that these metals are materials which exhibit excellent corrosion resistance and excellent compatibility with a living tissue in the same manner as titanium. Further, materials other than metals can be also used provided that the materials are non-flexible rigid materials which exhibit excellent corrosion resistance and excellent compatibility with a living tissue. For example, a synthetic resin may be used as a material for forming the first connection tubular body, the cylindrical tubular body and the second connection tubular body. In cases where the conduit forming unit according to the present invention is used at locations other than a ventricular assist system, the degree of freedom in selecting materials for forming the first connection tubular body, the cylindrical tubular body and the second connection tubular body is further increased.

(4) In the above-mentioned embodiment, the description has been made with respect to the conduit forming unit where the connection tubular bodies (first connection tubular body 220 and the second connection tubular body 230 in the case of the above-mentioned embodiment) are respectively connected to both end portions (the first end portion 212 and the second end portion 213) of the cylindrical tubular body 210 using the tube joints 100 (tube joints 100A, 100B). However, it is not always necessary for the conduit forming unit to have the configuration where the connection tubular bodies are respectively connected to both end portions of the cylindrical tubular body 210. For example, the conduit forming unit may have the configuration where the connection tubular body is connected to only one end portion (first end portion 212, for example) of the cylindrical tubular body 210 using the tube joint (tube joint 100A, for example).

The invention claimed is:

1. A conduit forming unit comprising:
a cylindrical tubular body where flanges are respectively formed on an outer peripheral surface of a first end portion of the cylindrical tubular body and on an outer peripheral surface of a second end portion of the cylindrical tubular body on a side opposite to the first end portion in an axial direction of a tubular body, the flanges being integrally formed on the tubular body in a protruding manner toward an outer side in a radial direction;
a first connection tubular body disposed on a first end portion side of the cylindrical tubular body, and having male threads on an outer peripheral surface of the first connection tubular body;
a second connection tubular body disposed on a second end portion side of the cylindrical tubular body, and having male threads on an outer peripheral surface of the second connection tubular body;
a tube joint which connects the cylindrical tubular body and the first connection tubular body to each other; and
a tube joint which connects the cylindrical tubular body and the second connection tubular body to each other, wherein
both the tube joint and the tube joint each include:
a cylindrical pawl equipped nut where female threads which are threadedly engageable with the male threads formed on the first connection tubular body or the male threads formed on the second connection tubular body are formed on an inner peripheral surface of the cylindrical pawl equipped nut, a plurality of pawl portions which are engageable with either of the flanges of the cylindrical tubular body are formed in the cylindrical pawl equipped nut in a circumferential direction and in a protruding manner toward an inside in a radial direction, the plurality of pawl portions are configured to get over the either of the flanges of the cylindrical tubular body and to engage with the either of the flanges, and the female threads are configured to threadedly engage with the male threads of the first connection tubular body or the male threads of the second connection tubular body so as to bring about a fastening state of the cylindrical pawl equipped nut thus enabling connection between the first connection tubular body and the cylindrical tubular body or connection between the second connection tubular body and the cylindrical tubular body; and
a retaining ring being annularly mountable on an outer peripheral surface of the pawl equipped nut, the retaining ring being capable of retaining engagement of the plurality of pawl portions with the either of the flanges of the cylindrical tubular body, and
the plurality of pawl portions of the pawl quipped nut are each formed on each of distal end portions of a plurality of protruding lugs formed on the pawl equipped nut in a protruding manner in an axial direction at a predetermined interval in a circumferential direction, and the plurality of protruding lugs have elasticity in a radial direction, and the retaining ring is annularly mounted on the plurality of protruding lugs, and the retaining ring is configured to impart a pressing force to the plurality of pawl portions in a radial direction in a state where the retaining ring is annularly mounted on the plurality of protruding lugs.

2. The conduit forming unit according to claim 1, wherein the first connection tubular body is connected to a left ventricle of a heart of a living body, and has a function of guiding blood flowing out from the left ventricle of the heart to the cylindrical tubular body, and
the second connection tubular body is provided to a blood pump of a ventricular assist system, and has a function of allowing the blood flowing out from the cylindrical tubular body to flow into the blood pump.

3. The conduit forming unit according to claim 1, wherein the cylindrical tubular body, the first connection tubular body and the second connection tubular body are each formed of a non-flexible rigid member.

4. The conduit forming unit according to claim 3, wherein the non-flexible rigid member is made of metal.

5. The conduit forming unit according to claim 1, wherein the first connection tubular body, the cylindrical tubular body and the second connection tubular body are formed such that, in a state where the first connection tubular body, the cylindrical tubular body and the second connection tubular body are connected to each other, an inner peripheral surface of the first connection tubular body, an inner peripheral surface of the cylindrical tubular body, and an inner peripheral surface of the second connection tubular body form a non-stepped surface in an axial direction.

6. The conduit forming unit according to claim 1, wherein an annular sealing member is interposed between the first connection tubular body and the cylindrical tubular body, and an annular sealing member is interposed between the second connection tubular body and the cylindrical tubular body.

7. The conduit forming unit according to claim 1, wherein in the plurality of pawl portions of the cylindrical pawl equipped nut, a surface of each of the pawl portions which faces the either of the flanges is a tapered surface inclined inward as the surface extends toward a center of the cylindrical pawl equipped nut in a radial direction.

8. The conduit forming unit according to claim 1, wherein recessed grooves are formed on respective outer peripheral surfaces of the plurality of protruding lugs in a circumferential direction, and a projection which engages with the recessed grooves is formed on an inner peripheral surface of the retaining ring.

9. A tube joint configured to be used for connecting: a cylindrical tubular body where flanges are respectively formed on an outer peripheral surface of a first end portion of the cylindrical tubular body and on an outer peripheral surface of a second end portion of the cylindrical tubular body on a side opposite to the first end portion in an axial direction of a tubular body, the flanges being integrally formed on the tubular body in a protruding manner toward an outer side in a radial direction; and a first connection tubular body disposed on a first end portion side of the cylindrical tubular body, and having male threads on an outer peripheral surface of the first connection tubular body,
the tube joint being also configured to be used for connecting: the cylindrical tubular body; and a second connection tubular body disposed on a second end portion side of the cylindrical tubular body, and having male threads on an outer peripheral surface of the second connection tubular body, the tube joint comprising:

a cylindrical pawl equipped nut where female threads which are threadedly engageable with the male threads formed on the first connection tubular body or the male threads formed on the second connection tubular body are formed on an inner peripheral surface of the cylindrical pawl equipped nut, a plurality of pawl portions which are engageable with either of the flanges of the cylindrical tubular body are formed in the cylindrical pawl equipped nut in a circumferential direction and in a protruding manner toward an inside in a radial direction, the plurality of pawl portions are configured to get over the either of the flanges of the cylindrical tubular body and engage with the either of the flanges, and the female threads are configured to threadedly engage with the male threads of the first connection tubular body or the male threads of the second connection tubular body so as to bring about a fastening state of the cylindrical pawl equipped nut thus enabling connection between the first connection tubular body and the cylindrical tubular body or connection between the second connection tubular body and the cylindrical tubular body; and a retaining ring being annularly mountable on an outer peripheral surface of the pawl equipped nut, the retaining ring being capable of retaining engagement of the plurality of pawl portions with the either of the flanges of the cylindrical tubular body, wherein the plurality of pawl portions of the pawl quipped nut are each formed on each of distal end portions of a plurality of protruding lugs formed on the pawl equipped nut in a protruding manner in an axial direction at a predetermined interval in a circumferential direction, and the plurality of protruding lugs have elasticity in a radial direction, and the retaining ring is annularly mounted on the plurality of protruding lugs, and the retaining ring is configured to impart a pressing force to the plurality of pawl portions in a radial direction in a state where the retaining ring is annularly mounted on the plurality of protruding lugs.

* * * * *